United States Patent [19]

Kamiya et al.

[11] Patent Number: 5,466,285
[45] Date of Patent: Nov. 14, 1995

[54] DENTAL PORCELAIN MATERIAL PREVENTING YELLOW COLORATION AND METHOD FOR PRODUCING SAME

[75] Inventors: Tadao Kamiya, Aichi; Motoyuki Inoue, Munakata; Hiroshi Inada, Nagoya, all of Japan

[73] Assignee: Noritake Co., Limited, Nagoya, Japan

[21] Appl. No.: 418,878

[22] Filed: Apr. 7, 1995

Related U.S. Application Data

[63] Continuation of Ser. No. 854,555, Mar. 19, 1992, abandoned.

[51] Int. Cl.⁶ .............................. C09K 3/00; C04B 35/00
[52] U.S. Cl. .................... 106/35; 433/218; 433/228.1; 501/6; 501/32; 501/14; 501/17
[58] Field of Search ............................. 106/35; 433/218, 433/229.1; 501/6, 32, 14, 17

[56] References Cited

FOREIGN PATENT DOCUMENTS

| | | |
|---|---|---|
| 310805 | 12/1988 | Japan . |
| 63-310805 | 12/1988 | Japan . |
| 3-812812 | 4/1991 | Japan . |
| 3-81212 | 4/1991 | Japan . |

OTHER PUBLICATIONS

Abstract of JP 03–005410 Jan. 11, 1991.
Abstract of JP 03–011005 Jan. 18, 1991.

*Primary Examiner*—C. Melissa Bonner
*Attorney, Agent, or Firm*—Fish & Richardson

[57] ABSTRACT

A dental porcelain material free of yellow coloring or opacification upon firing is produced. A powder mixture is prepared by adding 0.1 to 2.0 wt % of antimony trioxide and 0.01 to 5 wt % of nitric acid or its salt or salt, to a porcelain starting material. The powder mixture is heat-treated at a temperature not lower than the softening temperature of the powder mixture to produce a fused mass which is pulverized and water-washed. 0.01 to 5 wt % of nitric acid or its salt or salts may be added again during the pulverizing step.

29 Claims, No Drawings

DENTAL PORCELAIN MATERIAL PREVENTING YELLOW COLORATION AND METHOD FOR PRODUCING SAME

This application is a continuation of U.S. application Ser. No. 07/854,555, filed Mar. 19, 1992, now abandoned.

FIELD OF THE INVENTION

This invention relates to a dental porcelain material and a method for producing same, and, more particularly, to a method for producing dental porcelain material used under the presence of silver (Ag).

BACKGROUND OF THE INVENTION

Discussions of Related Art

Dental porcelain suffers from the phenomenon of being changed to yellowish color when fired to bond (baked) to a metallic frame containing particular metal components, above all, silver (Ag), or when fired in an environment in which such metal components co-exist. This phenomenon, referred to hereinafter as yellow coloration, is fatal to the dental porcelain, the color tone of which needs to be conditioned carefully after firing. Although various measures have so far been taken to eliminate this problem. None of these measures is fully satisfactory. Some of the defects inherent in these conventional measures are discussed hereinbelow.

Yellow coloration by silver is diminished to some extent by a method comprising placing carbon honeycomb and a carbon plate side by side with dental porcelain in a furnace. However, not only is it possible with this method to prevent yellow coloration completely, but the porcelain tends to be faded in color due to oxides under the reducing action caused by CO gas. In addition, air bubbles tend to be produced in the porcelain.

There has also been proposed a method consisting in previously coating a metallic conditioner on a porcelain-baking surface of a metallic frame or the like. However, with this method, the bonding strength of the porcelain to the frame tends to be lowered. Besides, silver is volatilized from the inside of a non-processed metallic frame or from the interior of the furnace contaminated with silver, so that yellow coloration of the porcelain can not be prevented completely. Besides, if the porcelain is post-brazed to an artificial crown formed of an Au—Pd—Ag alloy or a Pt—Au based alloy containing about 10% of silver, yellow coloration of the porcelain is unavoidably produced due to silver contained in these alloys.

If a metal frame is produced using semi-precious grade alloys free from silver, the porcelain fired to bond to the metal frame is hardly subjected to yellow coloration. However, if a silver-containing artificial cast crown is post-brazed to the metallic frame, yellow coloration is unavoidably produced at a boundary region. However, if the artificial crown is post-brazed to the metallic frame free of silver, the bonding strength is so low that fracture tends to be produced within the oral cavity. Thus, one is frequently obliged to prefer the method of firing the porcelain to bond to the silver-containing alloy frame to endure the phenomenon of yellow coloration.

Recently, a porcelain material containing nitrate compounds has been proposed, as in JP Patent KOKAI Publication No. 63-310805(1988). However, the resulting porcelain tends to suffer from opacification after firing. On the other hand, yellow coloration cannot be prevented satisfactorily if the porcelain is repeatedly subjected to firing. That is, although yellow coloration can be effectively prevented as long as the first firing is concerned, the nitrate compounds are dissipated by the initial firing and become hardly effective during the subsequent firing process so that yellow coloration is ultimately produced.

OBJECT AND SUMMARY OF THE INVENTION

It is therefore a principal object of the present invention to provide a novel dental porcelain material which does not cause yellow coloration or opacification and a method for producing the same.

It is another object of the present invention to provide a method for producing dental porcelain without causing yellow coloration or opacification even under repeated firing.

Other objects will become apparent in the entire disclosure.

According to the first aspect of the present invention, there is provided a method for producing dental porcelain material comprising:

providing a powder mixture by adding 0.1 to 2.0 wt % of powders of antimony trioxide and 0.01 to 5 wt % of nitric acid and/or a salt(s) thereof, based on the total weight of a porcelain starting material, to said porcelain starting material, heat-treating said powder mixture at a temperature not lower than the softening temperature of said powder mixture, to produce a fused mass, pulverizing said fused mass, and washing the pulverized fused mass with water.

According to the second aspect of the present invention, there is provided a dental porcelain material composition consisting essentially of a porcelain starting material, 0.1 to 2.0 wt % of antimony trioxide and 0.01 to 5 wt % of nitric acid and/or salt(s) thereof based on the total weight of the porcelain starting material. The composition may be in the form of particulated fused mass, preferably washed with water.

In a preferred embodiment of the present invention, 0.01 to 5 wt %, based on the total weight of the powder mixture, of nitric acid and/or a salt(s) thereof, may be added to the fused mass again during the pulverizing step. The resultant mass may be again fused, pulverized and washed with water.

Although the mechanism of preventing the yellow coloration by the above method has not been clarified precisely, it may possibly be surmised that, if the porcelain (glass) changed to yellow color by silver is heated to an elevated temperature of an order of 1200° C., the yellow tint is lost and the porcelain becomes transparent. If the transparent porcelain is again heated at a lower temperature of an order of 800° C., the porcelain again assumes a yellow color. Thus, yellow coloration is produced due to the fact that Ag which is in the state of Ag ions at elevated temperatures is turned into the state of an Ag colloid at lower temperatures to undergo coloration. However, if a predetermined amount of $Sb_2O_3$ is added to and contained in the porcelain material, a sort of an oxidizing action is produced to cause Ag dispersed in the porcelain to be present stably as Ag ions. Besides, by addition of a predetermined amount of nitric acid or a salt(s) thereof, referred to hereinafter as nitric acid etc., to the porcelain starting material, the surface of the porcelain material powders is inactivated to prevent the occurrence of yellow coloration. In addition, by heat treatment, nitric acid radicals are taken into a fused mass, which is in the state of a glass network, to assist in the action of preventing yellow coloration. Besides, the majority of the nitric acid radicals is dissipated as nitrogen oxides. Moreover, through the subsequent pulverizing step and the step of washing with water, any free radicals or residual nitrates can be removed positively to additionally prevent the porcelain layer from being opacified during firing. Besides, if the fused mass is again added with a predetermined amount of nitrates during the pulverizing step, and is subsequently washed with water, yellow coloration can be prevented more extensively, even upon repeated firing, due to inactivation of the surface of the porcelain material powders.

DESCRIPTION OF THE PREFERRED EMBODIMENTS

The amount of $Sb_2O_3$ is 0.1 to 2.0 wt % and preferably 1.0 wt % based on the amount of glass frits as the starting porcelain material. If the amount of $Sb_2O_3$ is less than 0.1 wt %, the effect of preventing yellow coloration is not obtained, whereas, if the amount exceeds 2.0 wt %, the porcelain suffers fluctuation in thermal expansion coefficients to cause hindrances at the time of firing the porcelain material to the metallic frame.

The particle size of $Sb_2O_3$ is preferably of the order of 5 to 10 μm.

Nitrates among nitric acid etc., are preferably salts of metals of the group 1A or the group 2A according to the subgroup naming of the Periodic Table of the International version, such as sodium nitrate, potassium nitrate, lithium nitrate, calcium nitrate, magnesium nitrate, barium nitrate or strontium nitrate. These are used alone or as a mixture and, usually, in the form of powders. Fine powders with a particle size of the order of 100 μm or less are preferred because a homogeneous mixture may be produced with this particle size. These nitrates are added in an amount of 0.01 to 5.0 wt %, preferably 0.1 to 2.0 wt %, based on the amount of the glass frits. If the amount of the nitrates is less than 0.01 wt %, the desired effect in preventing yellow coloration is not obtained, whereas, if the amount exceeds 5.0 wt %, the porcelain layer is opacified during firing of the porcelain layer backed to the metal frame.

As for the glass frits constituting the porcelain material, a composition customarily employed for the dental porcelain material may be employed. For example, the glass frits may have a basic composition of 55 to 67 wt % of $SiO_2$, 15 to 25 wt % of $Al_2O_3$, 8 to 10 wt % of $K_2O$ and 8 to 12 wt % of $Na_2O$. If necessary, oxides of elements of the groups 1A, 2A, 3B, 4B, such as, for example, $LiO_2$, $CaO$, $MgO$, $B_2O_3$ or $SnO_2$, or oxides of transition metals, such as $TiO_2$ or $ZnO$, or silicates such as $ZrSiO_4$, may be added to the basic composition. Colorants normally in use, such as oxides of Co, Cr, Mn, Al, Fe, V or Pt, or mixtures thereof, may be employed. Preferably, Pb is not to be used, because it is reacted with $Sb_2O_3$ to form a spinel compound to retard the yellow coloration preventive effect proper to $Sb_2O_3$, which then acts rather as a colorant.

As for adding $Sb_2O_3$ and nitric acid etc. to the glass frits, $Sb_2O_3$ may be added in the form of powders, for example, and the resulting mixture may then be ball-milled. $Sb_2O_3$ may also be added at the time of preparing the glass frit(s) by melting silica, alumina and alkali carbonates to give a predetermined composition. In this manner, the preparation of the glass frits and the addition of $Sb_2O_3$ may be effected simultaneously. However, it is not desirable to add nitric acid etc. at the time of preparing the glass frits because nitric acid etc. is turned into oxides through heating to a temperature of an order of 1400° C. for melting the glass frits so that the yellow coloration preventing effect proper to nitric acid etc. cannot be displayed.

The glass frit powder mixture is then heat-treated at a temperature not lower than the softening temperature of the powder mixture, usually 900° C., to effect crystallization. Nitric acid radicals are taken into a network of the crystallized glass formed of precipitated fine crystallites (e.g., leucite) to assist in the action of preventing the yellow coloration. The softening temperature is usually in the range of about 400° C. to about 800° C., although it may vary depending on the porcelain composition. On the other hand, the heat treatment is preferably carried out at a temperature which is the softening temperature plus 300° C. or less. The reason is that, if the heat treatment is carried out at a temperature higher than this range, the glass starts to be fluidized significantly to retard crystallization. Meanwhile, the heat treatment time may be suitably adjusted depending on the processing temperature and may be set so as to be in the range of e.g. 0.1 to 5 hours and preferably in the range of 0.5 to 1.0 hour.

The produced fused mass is pulverized and washed with water. In this manner, free nitrates not previously taken into the glass may be removed completely to reliably prevent opacification which might otherwise be produced at the time of firing of the porcelain. It is preferred that the average particle size of 20 to 30 μm be achieved by pulverization. The pulverized product is washed with water by passing the product in water through a filter, preferably several times, and removing a supernatant liquid. During the pulverizing step, nitric acid etc. may be added a second time to the mass during the pulverizing step, and the resulting mixture may then be washed with water, where by the yellow coloration preventing effect may be displayed even on repeated firing. It is noted that the composition of nitric acid etc. and the manner of addition thereof at the time of the second addition need not be the same as those at the time of the initial addition.

The porcelain starting material thus admixed with $Sb_2O_3$ and nitric acid etc. is placed and pressed into a built up mass in the usual manner on a metal substrate and the resulting assembly is fired repeatedly. The dental porcelain material may be applied to any of opaque, body, enamel or translucent porcelain material, while being effective as a margin porcelain material.

According to the present invention, by addition of predetermined amounts of $Sb_2O_3$ and nitric acid etc. and by effecting heat treatment in a predetermined manner, a porcelain layer having a predetermined color tone may be formed in a manner free from yellow coloration under any operating conditions including firing the porcelain layer to bond to the metal surface, repeated subsequent firing, postbrazing using a gold solder, and firing in a furnace contaminated with silver. Above all, since $Sb_2O_3$ remains after sintering, yellow coloration to the porcelain may be prevented effectively even when the porcelain is sintered repeatedly in a usual manner for use as dental porcelain. If nitric acid etc. are added a second time during the step of pulverization of a fused mass, yellow coloration on repeated sintering may be prevented more reliably. Besides, opacification may also be prevented despite the fact that nitric acid etc. is added to the porcelain starting material.

EXAMPLES

To glass frits, composed of 65.6 wt % of $SiO_2$, 15.0 wt % of $Al_2O_3$, 8.1 wt % of $K_2O$ and 10.5 wt % of $Na_2O$ and having a transition temperature of 525° C. and a particle size of 200 meshes or less, predetermined amounts of Sb$_2$O$_3$ having an average particle size of 5 μm, and nitric acid etc. were added by way of initial addition. The resulting mixture was heat-treated under the conditions shown in Table 1, and the resulting mass was pulverized in a ball mill to a particle size of 200 meshes or less and washed with water to produce porcelain material samples Nos. 1 to 15. Some of the samples (sample Nos. 7 to 12) were admixed with predetermined amounts of nitric acid etc. a second time during pulverization following the heat treatment (referred to as secondary addition).

Comparative Example

Porcelain material samples Nos. 16 and 17 were produced in the same manner as in Example above, except that Sb$_2$O$_3$ was not added and the washing with water was not carried out. It is noted that nitrate was added at the time of pulverizing the glass frits.

A representative commercially available porcelain material, produced by a Japanese producer A, was also procured as sample No. 18.

Comparative Test

The following tests were conducted on the samples Nos. 1 to 15 according to the Example and the samples Nos. 16 to 18 according to the Comparative Example.

Test A

The porcelain material samples were pressed in a metal mold, each to a disk 12 mm in diameter and 2 mm in thickness. 5 mg of pure silver powders were placed at the center of the disks and the resulting assemblies were fired under the following various firing conditions to check as to whether or not and to what degree the samples underwent yellow coloration and opacification.

The following firing conditions were used:

1) silver powders were placed at the center of the disks and the resulting assemblies were sintered at 920° C. which is the standard firing temperature for the porcelain material;

2) silver powders were placed at the center of the disks and the resulting assemblies were repeatedly fired five times at the above mentioned standard temperature; and 3) silver powders were placed at the center of the disks and the resulting assemblies were repeatedly fired ten times at the above mentioned standard temperature.

The results are also shown in Table 1.

TABLE 1

| Sample Nos. | Initial addition (%) | | | Heat treatment | Secondary addition (%) | | | Processing with water | Test piece (yellow damage/ opacification) | | | Bridg (yellow damage/ opacification) | | |
|---|---|---|---|---|---|---|---|---|---|---|---|---|---|---|
| | Sb$_2$O$_3$ | KNO$_3$ | NaNO$_3$ | | NH$_4$NO$_3$ | KNO$_3$ | NaNO$_3$ | | 1st | 5th | 10th | 1st | 5th | 10th |
| 1 | 0.26 | | | 900° C. × 1H | | | | Processed | O/O | O/O | Δ/O | O/O | O/O | Δ/O |
| 2 | | 0.08 | | 850° C. × 2 | | | | " | O/O | O/O | Δ/O | O/O | O/O | Δ/O |
| 3 | | | 1.52 | 900° C. × 2 | | | | " | O/O | O/O | Δ/O | O/O | O/O | Δ/O |
| 4 | 0.36 | 1.67 | | 920° C. × 3 | | | | " | O/O | O/O | Δ/O | O/O | O/O | Δ/O |
| 5 | 0.26 | | 0.35 | 850° C. × 2 | | | | " | O/O | O/O | Δ/O | O/O | O/O | Δ/O |
| 6 | 1.52 | 0.68 | 0.58 | 960° C. × 2 | | | | " | O/O | O/O | Δ/O | O/O | O/O | Δ/O |
| 7 | 0.50 | | | 900° C. × 2 | 0.25 | | | " | O/O | O/O | O/O | O/O | O/O | O/O |
| 8 | | 3.62 | | 850° C. × 1 | | 1.25 | | " | O/O | O/O | O/O | O/O | O/O | O/O |
| 9 | | | 2.58 | 950° C. × 2 | | | 0.08 | " | O/O | O/O | O/O | O/O | O/O | O/O |
| 10 | 0.28 | 1.26 | | 900° C. × 1 | | 2.20 | 1.25 | " | O/O | O/O | O/O | O/O | O/O | O/O |
| 11 | 1.25 | | 1.35 | 950° C. × 1 | 1.58 | | 0.54 | " | O/O | O/O | O/O | O/O | O/O | O/O |
| 12 | 0.25 | 0.85 | 0.45 | 900° C. × 1 | 0.58 | 1.58 | 2.25 | " | O/O | O/O | O/O | O/O | O/O | O/O |
| 13 | | 6.23 | | 900° C. × 1 | | | | " | O/X | O/X | Δ/X | O/X | O/X | Δ/X |
| 14 | 0.05 | 0.005 | | 900° C. × 1 | | | | " | Δ/O | X/O | X/O | Δ/O | X/O | X/O |
| 15 | | | 1.25 | 450° C. × 1 | | | | " | O/X | O/X | Δ/X | O/X | O/X | Δ/X |
| *16 | | | | | 0.84 | | | Not processed | Δ/X | Δ/X | Δ/X | Δ/X | Δ/X | Δ/X |
| *17 | | | | | | 1.54 | | Not processed | Δ/X | Δ/X | Δ/X | Δ/X | Δ/X | Δ/X |
| *18 | | | | | | | | | X/O | X/O | X/O | X/O | X/O | X/O |

*Comparative Example

TABLE 1-continued

| Sample | Initial addition (%) | | | | Secondary addition (%) | | | Processing with | Test piece (yellow damage/ opacification) | | | Bridg (yellow damage/ opacification) | | |
|---|---|---|---|---|---|---|---|---|---|---|---|---|---|---|
| Nos. | Sb$_2$O$_3$ | KNO$_3$ | NaNO$_3$ | Heat treatment | NH$_4$NO$_3$ | KNO$_3$ | NaNO$_3$ | water | 1st | 5th | 10th | 1st | 5th | 10th |

O: No yellow damaging (or opacification)
Δ: Slight yellow damaging (or opacification)
X: Considerable yellow damaging (or opacification)

It is seen from Table 1 that the Samples Nos. 16 to 18 of the Comparative Example underwent yellow coloration or opacification under the above mentioned firing conditions. On the contrary, the samples Nos. 7 to 12 of the Example, containing predetermined amounts of Sb$_2$O$_3$ and nitric acid etc., which were heat-treated in a predetermined manner and which were admixed with nitric acid etc. at the time of pulverization, showed no yellow coloration or opacification under any of the operating conditions.

The results on sample No. 14 indicate that yellow coloration was brought about when the amount of Sb$_2$O$_3$ is lower than a predetermined value (0.1 wt %).

Also the results on sample No. 14 indicate that yellow coloration was brought about when the amount of nitric acid etc. is less than 0.01 wt %, while the results on sample No. 13 indicate that opacification is caused when the amount of nitric acid etc. exceeds 5.0 wt %.

The results on sample No. 15 indicate that opacification is also caused when heat treatment is carried out at a temperature lower than the softening temperature.

The results on sample Nos. 1 to 6 indicate that, unless nitric acid etc. is added during the pulverizing step, sufficient effects on yellow coloration cannot be produced on repeated firing.

Test B

Metal frames of a triple bridge and a single artificial crown were produced from an alloy E-U (0.5 wt % Pt-58 wt % Pd-29 wt % Ag), a commercially available semi-precious alloy which causes the severest yellow coloration. Porcelain material samples Nos. 1 to 18 were placed and pressed into built up masses on metal frames, and the resulting assemblies were fired. The fired metal frame and an artificial crown of an Au—Pd—Ag alloy were brazed together in a furnace by a gold solder containing silver (Ag). The porcelain layer, directly after firing, was checked as to whether or not and to which extent yellow coloration and opacification were produced. The results are also shown in Table 1.

It is seen from Table 1 that the samples Nos. 16 to 18 underwent considerable yellow coloration or opacification. On the contrary, with the samples Nos. 1 to 12 of the Example containing predetermined amounts of Sb$_2$O$_3$ and nitric acid etc., heat-treated in a predetermined manner, yellow coloration or opacification were scarcely observed when the samples were fired to bond to Ag-containing metal frames in the form of the single artificial crown or bridge.

The results on the samples Nos. 13 to 15 indicate that, unless the amount of nitric acid etc. and the softening temperature are maintained within predetermined ranges, yellow coloration and white opacification are produced in the course of firing of the porcelain samples for bonding to the Ag-containing frames. The results on samples Nos. 1 to 6 also indicate that, unless nitric acid etc. is added during the pulverizing step, yellow coloration can be prevented only insignificantly.

Although the foregoing description has been made of the dental porcelain, similar favorable results may be obtained with other vitreous compositions, such as decorative products.

If should be noted that modifications obvious in the art may be done without departing from the gist and scope herein disclosed and claimed by the appended claims.

What is claimed is:

1. A method for producing a dental porcelain material comprising:

providing a powder mixture by adding to a porcelain starting frit material 0.1 to 2.0 wt % of powders of antimony trioxide and 0.01 to 5 wt % of at least one nitric acid component selected from the group consisting of nitric acid and salts thereof, based on the total weight of the porcelain starting frit material, heat-treating said powder mixture at a temperature not lower than the softening temperature of said powder mixture to produce a fused mass, and pulverizing and water-washing said fused mass in which 0.01 to 5 wt %, based on the total weight of the powder mixture, of at least one further nitric acid component selected from the group consisting of nitric acid and salts thereof is further added to said fused mass during said pulverizing step, said dental porcelain material having resistance to yellow coloration after repeated firings exceeding at least five times.

2. The method as defined in claim 1, in which said salts are selected from the group consisting of nitrates of elements of IA and IIA subgroup of the International Periodic Table.

3. The method as defined in claim 1, in which said at least one nitric acid component selected from the group consisting of nitric acid and salts thereof is added in an amount of 0.1 to 2.0 wt % based on the porcelain starting frit material.

4. The method as defined in claim 1, in which the heat treatment is carried out at a temperature above the softening temperature of the porcelain starting frit material.

5. The method as defined in claim 4, in which the heat treatment is carried out at a temperature range not higher than by 300 degrees C. above the softening temperature.

6. The method as defined in claim 4, in which the heat treatment is carried out at about 900 degrees C.

7. The method as defined in claim 1, in which antimony trioxide is initially incorporated with the porcelain starting frit material upon melting to a glass frit.

8. The method as defined in claim 1, in which the porcelain starting frit material is a glass frit having a softening point approximately of 400 to 800 degrees C.

9. The method as defined in claim 1, in which the porcelain starting frit material is a glass frit having a basic composition of 55 to 67% SiO$_2$, 15 to 25% Al$_2$O$_3$, 8 to 10% K$_2$O and 8 to 12% Na$_2$O by weight percents.

10. The method as defined in claim 9, in which the porcelain starting frit material is free of Pb.

11. The method as defined in claim 9, in which the porcelain starting frit material further comprises at least one selected from the group consisting of oxides of elements of the subgroups IA, IIA, IIIB and IVB of the International Periodic Table.

12. The method as defined in claim 9, in which the porcelain starting frit material further comprises at least one oxide selected from the group consisting of $LiO_2$, CaO, MgO, $B_2O_3$, $SnO_2$, $TiO_2$, ZnO and $ZrSiO_4$.

13. The method as defined in claim 9, in which the porcelain starting frit material further comprises at least one oxide coloring agent selected from the group consisting of oxides of Co, Cr, Mn, Al, Fe, V and Pr.

14. A method for producing a dental porcelain material comprising:

providing a powder mixture by adding to a porcelain starting frit material 0.1 to 2.0 wt % of powders of antimony trioxide and 0.01 to 5 wt % of at least one nitric acid component selected from the group consisting of nitric acid and salts thereof, based on the total weight of the porcelain starting frit material, heat-treating said powder mixture at a temperature not lower than the softening temperature of said powder mixture to produce a fused mass, and pulverizing and water-washing said fused mass in which 0.01 to 5 wt %, based on the total weight of the powder mixture, of at least one further nitric acid component selected from the group consisting of nitric acid and salts thereof is further added to said fused mass during said pulverizing step.

15. A dental porcelain material consisting essentially of a porcelain starting frit material and 0.1 to 2.0 wt % of antimony trioxide and 0.01 to 5 wt % of at least one nitric acid component selected from the group consisting of nitric acid and salts thereof, based on the total weight of a porcelain starting frit material, said dental porcelain material having resistance to yellow coloration after at least ten firings.

16. The dental porcelain material as defined in claim 15, in which said salts are selected from the group consisting of nitrates of elements of IA and IIA subgroup of the International Periodic Table.

17. The dental porcelain material as defined in claim 15, in which said at least one nitric acid component selected from the group consisting of nitric acid and salts thereof is present in an amount of 0.1 to 2.0 wt % based on the porcelain starting frit material.

18. The dental porcelain material as defined in claim 15, in which the porcelain starting frit material is a glass frit having a softening point approximately of 400 to 800 degrees C.

19. The dental porcelain material as defined in claim 15, in which the porcelain starting frit material is a glass frit having a basis composition of 55 to 67% $SiO_2$, 15 to 25% $Al_2O_3$, 8 to 10% $K_2O$ and 8 to 12% $Na_2O$ by weight percents.

20. The dental porcelain material as defined in claim 19, in which the porcelain starting frit material is free of Pb.

21. The dental porcelain material as defined in claim 19, in which the porcelain starting frit material further comprises at least one oxide selected from the group consisting of oxides of elements of the subgroups IA, IIA, IIIB and IVB of the International Periodic Table.

22. The dental porcelain material as defined in claim 19, in which the porcelain starting frit material further comprises at least one oxide selected from the group consisting of $LiO_2$, CaO, MgO, $B_2O_3$, $SnO_2$, $TiO_2$, ZnO and $ZrSiO_4$.

23. The dental porcelain material as defined in claim 19, in which the porcelain starting frit material further comprises at least one oxide coloring agent selected from the group consisting of oxides of Co, Cr, Mn, Al, Fe, V and Pr.

24. The dental porcelain material as defined in claim 15, in which said material has been subjected to heat-treating at a temperature not lower than the softening temperature of a powdery mixture of said material.

25. The dental porcelain material as defined in claim 23, in which the heat treatment has been carried out at a temperature above the softening temperature of the porcelain starting frit material.

26. The dental porcelain material as defined in claim 24, in which the heat treatment has been carried out at a temperature range not higher than by 300 degrees C. above the softening temperature.

27. The dental porcelain material as defined in claim 24, in which the heat treatment has been carried out at about 900 degrees C.

28. The dental porcelain as defined in claim 24, in which antimony trioxide has been initially incorporated with the porcelain starting frit material upon melting to a glass frit.

29. The dental porcelain material as defined in claim 24, in which said fused mass further contains 0.01 to 5 wt %, based on the total weight of the powder mixture, of at least one further nitric acid component selected from the groups consisting of nitric acid and salts thereof.

* * * * *